US006216539B1

(12) United States Patent
Johnson et al.

(10) Patent No.: US 6,216,539 B1
(45) Date of Patent: Apr. 17, 2001

(54) EQUIPMENT SETUP FOR ULTRASONIC MONITORING

(75) Inventors: William S. Johnson; Rexford A. Battenberg, both of Knoxville, TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 09/197,898

(22) Filed: Nov. 23, 1998

(51) Int. Cl.$^7$ .................................................... G01N 29/00
(52) U.S. Cl. ............................. 73/592; 73/658; 73/661; 73/40.5 AO; 73/660; 73/593; 364/550
(58) Field of Search ............................ 73/649, 658, 659, 73/660, 661, 602, 40.5 A, 592, 593; 364/552, 550

(56) References Cited

U.S. PATENT DOCUMENTS

| | | | |
|---|---|---|---|
| 3,222,635 | 12/1965 | Simpkins et al. | 340/15 |
| 3,592,967 | 7/1971 | Harris | 179/1 A |
| 3,782,180 | 1/1974 | Harris | 73/69 |
| 3,978,915 | 9/1976 | Harris | 165/11 |
| 4,201,087 | 5/1980 | Akita et al. | 73/339 A |
| 4,416,145 | 11/1983 | Goodman et al. | 73/40.5 |
| 4,476,706 | 10/1984 | Hadden et al. | 73/1 G |
| 4,520,674 * | 6/1985 | Canada et al. | 73/660 |
| 4,612,620 * | 9/1986 | Davis et al. | 73/660 |
| 4,722,224 | 2/1988 | Scheller et al. | 73/599 |
| 4,823,600 | 4/1989 | Biegel et al. | 73/592 |
| 4,852,390 | 8/1989 | Fisch | 73/40.5 |
| 4,879,546 | 11/1989 | Dunham et al. | 340/632 |
| 4,945,766 | 8/1990 | Dahlmann et al. | 73/598 |
| 4,981,044 | 1/1991 | Adams et al. | 73/623 |
| 5,053,747 | 10/1991 | Slate et al. | 340/507 |
| 5,351,544 | 10/1994 | Endo et al. | 73/588 |
| 5,435,168 * | 7/1995 | Granere | 73/663 |
| 5,453,932 | 9/1995 | Brabec | 364/424.07 |
| 5,511,425 * | 4/1996 | Kleinert | 73/627 |
| 5,650,943 * | 7/1997 | Powell et al. | 73/40 |

\* cited by examiner

Primary Examiner—Hezron Williams
Assistant Examiner—Nashmiya Fayyaz
(74) Attorney, Agent, or Firm—Luedeka, Neely & Graham, P.C.

(57) ABSTRACT

An apparatus and method determines ultrasonic measurement parameters of ultrasonic measurements to be performed on a mechanical system, where the ultrasonic measurements are performed using a portable ultrasonic measurement device. The ultrasonic measurement parameters consist of information used in configuring the portable ultrasonic measurement device to make the ultrasonic measurements. The measurement parameters are used to configure an ultrasonic measurement device that uses an ultrasonic sensor to measure ultrasonic characteristics of the mechanical system, where the ultrasonic characteristics are indicative of an operating condition of the mechanical system. The apparatus includes a processor for generating user instruction messages that query a user concerning specific characteristics of the mechanical system on which the ultrasonic measurements are to be performed. The user instruction messages also provide response options from which the user chooses in responding to the instruction messages. The apparatus includes a user communication device that receives the user instruction messages generated by the processor, and communicates the user instruction messages to the user. A user input device enables the user to choose from among the response options, and generates user input signals based upon response options chosen by the user. The processor receives the user input signals and generates the ultrasonic measurement parameters based on the user input signals. A memory receives and stores the ultrasonic measurement parameters. An interface receives the ultrasonic measurement parameters from the processor. The interface is capable of transferring the ultrasonic measurement parameters from the processor to the portable ultrasonic measurement device.

22 Claims, 7 Drawing Sheets

EQUIPMENT SETUP FOR ULTRASONIC MONITORING

TECHNICAL FIELD

The present invention is generally directed to monitoring ultrasonic sound waves emanating from a mechanical system. The invention is more particularly directed to a device that determines appropriate measurement parameters to use in configuring an ultrasonic measurement instrument based upon the type of mechanical system to be monitored.

BACKGROUND OF THE INVENTION

Most industrial processes, including almost all sources of friction, create some ultrasonic noise. For example, leaks in pipes, machinery defects, and electrical arcing produce ultrasonic sound waves. When the intensity of such ultrasonic noise exceeds an expected or "normal" level, this is an indication of a possible fault in the mechanical or electrical system. Thus, by continuously or periodically monitoring the intensity of ultrasonic noise produced by industrial machinery, maintenance personnel can detect faults and initiate appropriate repairs.

Current ultrasonic measurement instruments employ electroacoustical transducers to convert ultrasonic sound waves into ultrasonic electrical signals. Most of these instruments include circuitry that converts the ultrasonic electrical signals into audio-frequency electrical signals that are within the range of frequencies that can be detected by the human ear. The typical instruments employ headphones that convert the audio electrical signals into sound for an operator to hear.

The SonicScan ultrasonic measurement instrument, manufactured by Computational Systems, Inc., converts the ultrasonic electrical signals into digital electrical signals that can be displayed to the operator in a digital format and stored in computer memory. It is controlled by a microprocessor, and can be programmed to perform ultrasonic measurements that are specifically tailored to detect a specific type of fault on a particular type of machine or at a particular location on a machine. Further, the microprocessor can be programmed to configure the instrument for optimum performance with different types of transducers, such as contact and noncontact transducers.

As described in a pending application (U.S. Ser. No. 09/073,276, filed May 5, 1998), the SonicScan instrument system employs a route-based ultrasonic monitoring method. The system preferably uses a central computer that stores testing information concerning which machines to test, such as within a manufacturing plant, and that stores measurement parameters used to configure a portable ultrasonic sensing instrument. At the appropriate time, the testing information is loaded from the central computer into a portable, hand-held processing and storage unit, such as a personal data assistant (PDA). An operator is then prompted by the PDA to proceed to a test location. Once at the test location, the PDA provides the testing information and measurement parameters to the portable ultrasonic sensing instrument. The test is then performed by the operator with the portable ultrasonic sensing instrument, and the test results are downloaded from the portable sensing instrument to the PDA. Once all the tests along a particular route of testing locations have been performed, the test results are downloaded from the PDA to the central computer. In this manner, the results of the most recent set of tests can be compared to the results of previous tests to determine whether any machinery defects are present.

SUMMARY OF THE INVENTION

The route-based system described above provides an advantageous means for guiding an operator along a testing route and configuring a portable ultrasonic instrument to perform the appropriate tests at each machine along the route.

The present invention is an improvement that aids an operator in the field in determining, based on the type of mechanical system to be tested, what type of ultrasonic monitoring should be performed for effective fault detection. Also, it guides the operator in selecting appropriate measurement parameters to configure an ultrasonic sensing instrument in the field for making ultrasonic measurements.

It further stores a record of the types and locations of the machines that are tested, and stores the measurement parameters that are used in configuring the ultrasonic sensing instrument for each measurement.

In accordance with the present invention, an apparatus and method determines ultrasonic measurement parameters of ultrasonic measurements to be performed on a mechanical system, where the ultrasonic measurements are to be performed using a portable ultrasonic measurement device. The ultrasonic measurement parameters include information used in configuring the portable ultrasonic measurement device to make the ultrasonic measurements. The measurement parameters are used to configure an ultrasonic measurement device that uses an ultrasonic sensor to measure ultrasonic characteristics of the mechanical system. The ultrasonic characteristics are indicative of an operating condition of the mechanical system.

The apparatus includes a processor for generating user instruction messages. The user instruction messages query a user of the apparatus concerning specific characteristics of the mechanical system on which the ultrasonic measurements are to be performed. The user instruction messages also provide response options from which the user chooses in responding to the instruction messages. The apparatus also includes a user communication device connected to the processor. The user communication device receives the user instruction messages generated by the processor, and communicates the user instruction messages to the user. Also connected to the processor is a user input device that enables the user to choose from among the response options, and generates user input signals based upon response options chosen by the user. The processor receives the user input signals and selects the ultrasonic measurement parameters to be measured based on the user input signals. A memory is connected to the processor for receiving and storing the ultrasonic measurement parameters. The apparatus also includes an interface connected to the processor for receiving the ultrasonic measurement parameters from the processor. The interface is capable of transferring the ultrasonic measurement parameters from the processor to the portable ultrasonic measurement device.

Thus, the present invention assists the user of the ultrasonic measurement device in determining, particularly in the field, the appropriate set of measurement parameters to use in configuring the ultrasonic measurement device. The apparatus and method does so by querying the user about the type of mechanical system to be tested, and then determining the appropriate parameters based upon the user's responses to the queries. Therefore, the user does not have to possess specialized knowledge concerning how to configure the ultrasonic measurement device for making the measurement. The user only needs to know the type of mechanical system on which the measurement is to be performed.

Further, once the ultrasonic measurement parameters have been determined, the present invention enables the user to configure the ultrasonic measurement device by downloading the measurement parameters to the measurement device via the interface. The user can also download the measurement parameters to a central computer.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIG. 8 is a view of a screen showing a Leak Detection Data dialog box;

FIG. 9 is a view of a screen showing a Valve Data dialog box;

FIG. 10 is a view of a screen showing a Mechanical Data dialog box;

DETAILED DESCRIPTION OF THE PREFERRED EMBODIMENT

Figure 1:
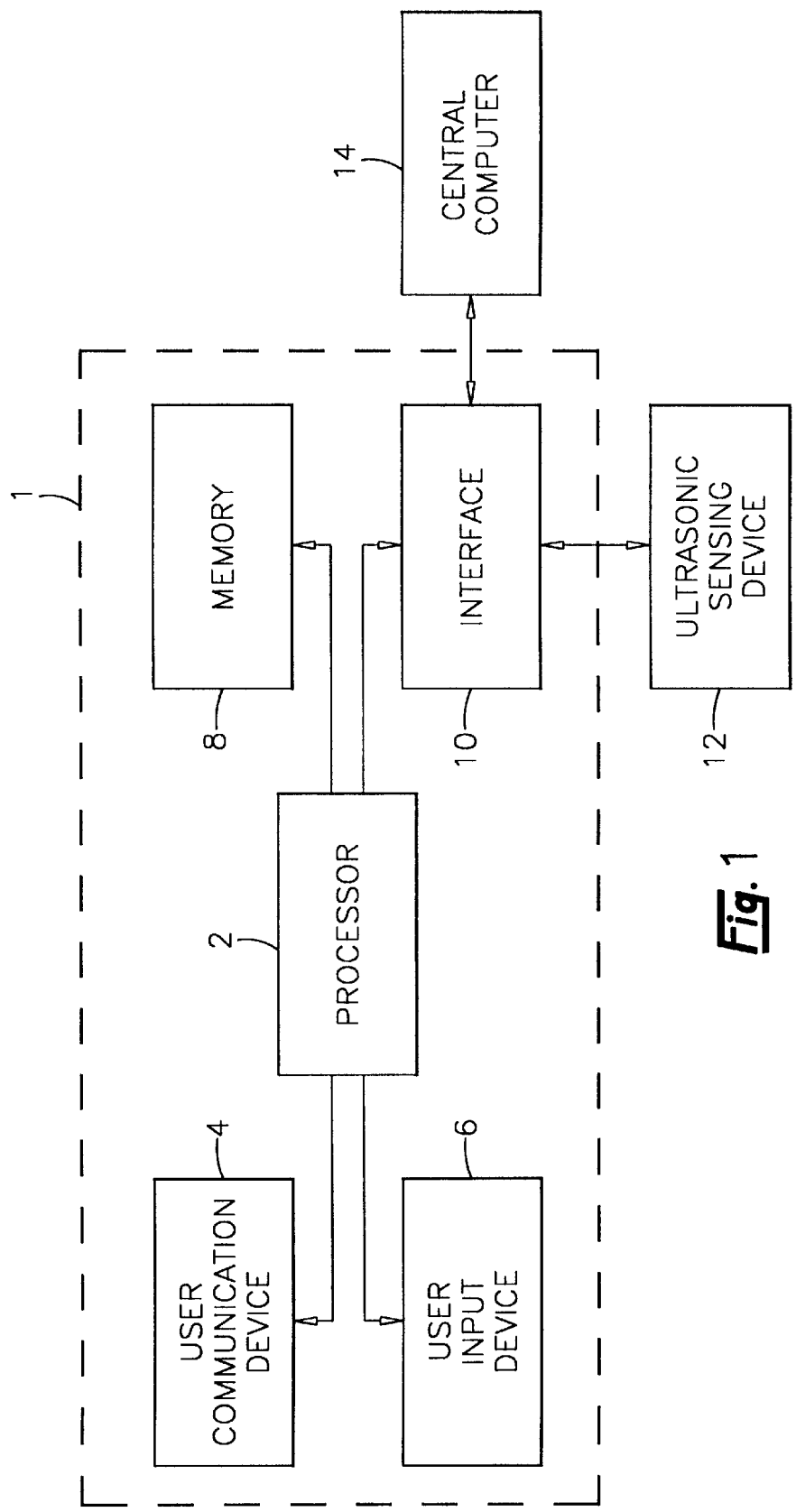
FIG. 1 is a functional block diagram of a preferred embodiment of the invention.

Shown in FIG. 1 is a block diagram of a preferred embodiment of a setup device 1 particularly useful for performing in-field configuration of a portable ultrasonic sensing device 12. Preferably, the setup device 1 is a hand-held, portable device, such as a personal data assistant (PDA) or a laptop computer. While portability is desirable, the invention is not limited to a portable device. The functions described below may also be performed on a device that is larger and less portable than a PDA.

With reference to FIG. 1, the setup device 1 includes a processor 2 that performs a number of functions, as described in greater detail hereinafter, by executing a set of software instructions. These functions include generating user instruction messages, receiving user input signals, and generating ultrasonic measurement parameters and alarm limits.

A user communication device 4 is connected to the processor 2. In a preferred embodiment of the invention, the user communication device 4 is a liquid crystal display (LCD) panel, or other flat-panel display device. The user communication device 4 has sufficient display area and resolution to generate a visual display that is legible to a user under normal operating conditions. As described below, the user communication device 4 receives user instruction messages from the processor 2 and communicates these messages to the user in a graphical or alphanumeric format. For example, the user communication device 4 may display to the user a list of possible machine types for the user to choose from in setting up a particular measurement.

With continued reference to FIG. 1, a user input device 6 is connected to the processor 2. The user input device 6 of the preferred embodiment includes an alphanumeric keyboard that the user uses to generate user input signals in response to user instruction messages displayed on the user communication device 4. The user input device 6 also includes arrow keys that allow the user to navigate among options presented to the user on the user communication device 4. Preferably, the user input device 6 is integrated with the user communication device 4 to provide a "touch screen" function. With the touch screen, the user chooses among response options presented to the user on the flat-panel display of the user communication device 4 by simply making contact with the flat-panel display using a pointing device. Thus, in the preferred embodiment, the user input device 6 includes an alphanumeric keyboard, arrow keys, and a touch screen to generate user input signals that are sent to the processor 2.

The processor 2 receives the user input signals from the user input device 6 and generates ultrasonic measurement parameters based upon the user input signals. For example, if the user responds to the user instruction messages by selecting a particular type of machine from among options presented on the user communication device 4, the processor 2 generates the appropriate measurement parameters for configuring the ultrasonic sensing device 12 to monitor that particular machine.

Preferably, the measurement parameters are stored in memory 8 connected to the processor 2. Contained within the memory 8 are sets of measurement parameters that are used to configure the ultrasonic sensing device 12 to make several different types of ultrasonic measurements on several different types of machines and mechanical systems. As described in greater detail hereinafter, the sets of measurement parameters are associated in memory 8 with generic types of mechanical systems or are associated with specific machines or mechanical systems. In the preferred embodiment, the memory 8 is a nonvolatile random access memory (NVRAM) device.

As shown in FIG. 1, an interface 10 is connected to the processor 2. The interface 10 may be a serial or parallel interface, or as in the preferred embodiment, the interface 10 is a wireless infrared interface. The interface 10 is capable of transferring information between the processor 2 and the ultrasonic sensing device 12, or between the processor 2 and a central computer 14. As explained in greater detail below, prior to making an ultrasonic measurement, the user transfers measurement parameters from the processor 3 to the ultrasonic measurement instrument 12 across the interface 10. The interface 10 is also used to transfer measurement parameters and measurement data from the processor 2 to the central computer 14.

Following is a description of the operation of the invention in a typical use situation. It is assumed for purposes of the following description that the user is setting up to make the first ultrasonic measurement on a particular mechanical system in an industrial setting. It is assumed that no previous configuration information exists for the mechanical system, and that the user is using the invention to generate the initial measurement parameters and identification information for the mechanical system. In other words, the following description assumes that the machine to be tested is not included in an existing measurement route, and is thus an "off-route" machine.

Figure 2:
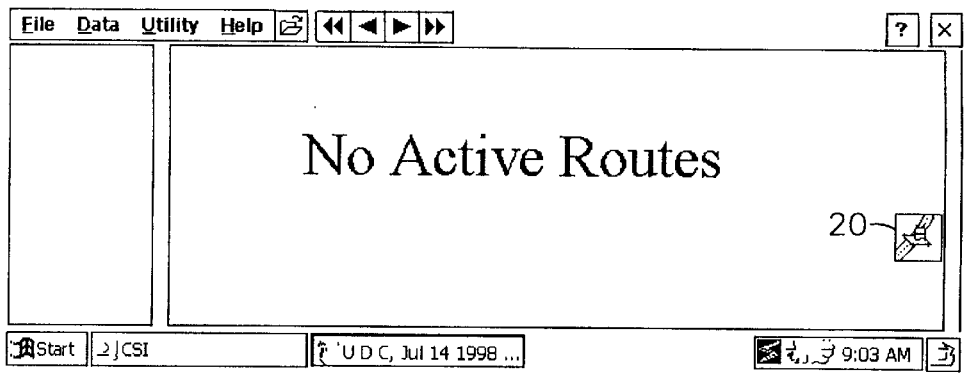
FIG. 2 is a view of a Main screen generated by the invention.

When the user turns on the setup device 1, the processor 2 sends a user instruction message to the user communication device 4. The user instruction message appears on the display of the user communication device 4 in the form of the graphic, or screen, shown in FIG. 2. As FIG. 2 indicates, there are no active routes currently selected by the setup device 1. Although there may be information stored in the memory 8 for preexisting measurement routes, none are currently selected. To set up measurement parameters for a machine that is not yet assigned to any preexisting route, the user "presses" (or "clicks on") the On/Off-route button 20 using the user input device 6. When the user presses the button 20, the setup device 1 enters an off-route mode. Thus, the On/Off-Route button 20 allows the operator to toggle between off-route and on-route modes.

Figure 3:
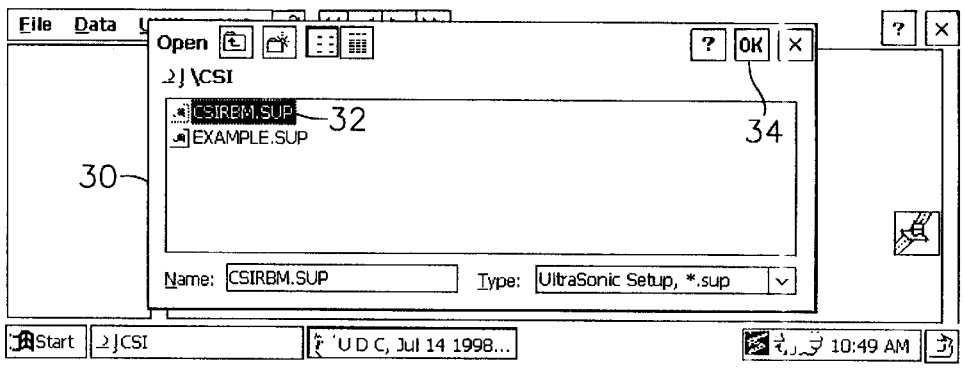
FIG. 3 is a view of a screen showing an Open dialog box.

When the user presses the button 20, the user input device 6 generates a user input signal that is sent to the processor 2. Based on the received user input signal, the processor 2 generates a user instruction message that appears on the user communication device 4 in the form of the "Open" dialog box 30 as shown in FIG. 3. In the example shown in FIG. 3, the "Open" dialog box 30 gives the user a choice of accessing one of two existing ultrasonic setup files, CSIRBM.SUP or EXAMPLE.SUP. These setup files contain ultrasonic measurement parameters that have been previously defined for specific or generic mechanical systems. For example, an ultrasonic setup file may contain the identification information, ultrasonic measurement parameters, and alarm limits for specific machines on a preexisting route. Alternatively, an ultrasonic setup file may contain suggested measurement parameters and alarm limits for generic mechanical systems, such as a generic valve or steam trap. For the purposes of this description, it has been assumed that no preexisting routes exist. Therefore, the user chooses to open the CSIRBM.SUP file 32 which contains suggested (default) measurement parameters and alarm limits for several generic mechanical systems. To open the file, the user highlights the selected file using the user input device 6 and then presses the OK button 34. When the OK button 34 is pressed, the user input device 6 generates an user input signal that causes the processor 2 to access the selected setup file from memory 8.

After the selected setup file is opened, the processor 2 reads the setup information from the selected setup file. In this example, the setup file contains measurement parameters for setting up the ultrasonic sensing device 12 to make measurements on a generic piping system, a generic roots valve, and a generic steam trap. Since the setup file contains multiple predefined setups to choose from, the processor 2 sends a user instruction message to the user communication device 4 giving the user a choice of generic equipment setups. The user instruction message appears on the display in the form of the "Select the Type of Equipment" dialog box 40 as shown in FIG. 4.

Note that the dialog box 40 also presents the user with a <New User Defined Machine> option 42. If the user chooses the option 42, the user will be guided through a process of setting up user-defined ultrasonic measurement parameters as explained in greater detail hereinafter.

Figure 5:
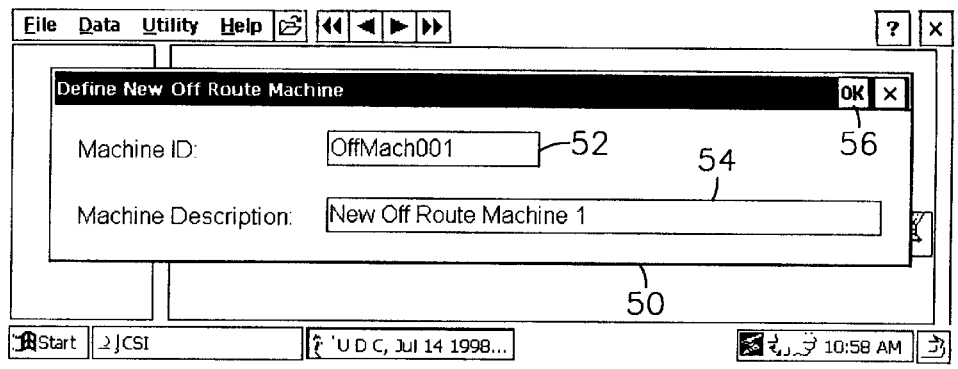
FIG. 5 is a view of a screen showing a Define New Off Route Machine dialog box.

Regardless of whether the user selects the <New User Defined Machine> option 42 or one of the generic setups, when the user presses the OK button 44, the screen as shown in FIG. 5 appears on the user communication device 4. The "Define New Off Route Machine" dialog box 50 allows the user to enter a machine identification string and a machine description. As shown in FIG. 5, the dialog box 50 includes a "Machine ID" input box 52 and a "Machine Description" input box 54, each having a default string of characters in the box. The user may change the default identification string or the default description by typing in new strings of characters using the user input device 6. When the user presses the OK button 56, the processor 2 enters the machine identification and description strings into memory 8.

Figure 4:
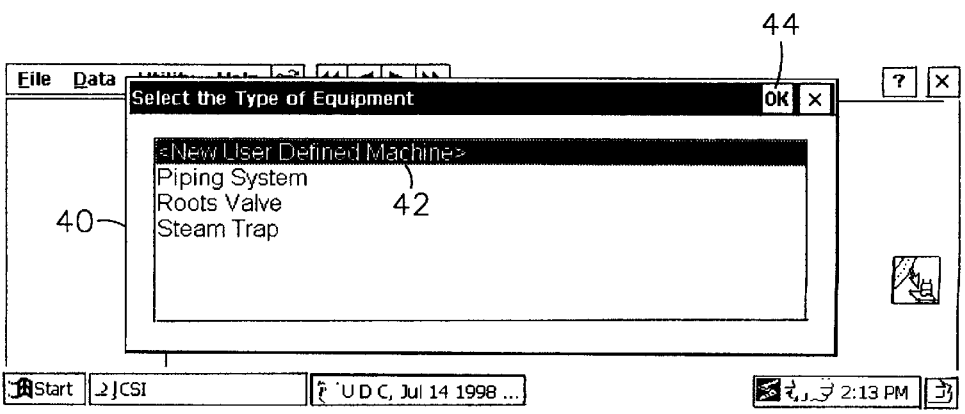
FIG. 4 is a view of a screen showing a Select the Type of Equipment selection box.

If the user had selected any of the three predefined generic setups from the dialog box 40 shown in FIG. 4, then when the OK button 56 is pressed, the processor 2 associates the ultrasonic measurement parameters in the selected generic setup with the machine identification string and description entered in dialog box 50. At this point, the processor 2 sends a user instruction message to the user communication device 4 in the form of the screen shown in FIG. 13. The response options presented by that screen will be discussed in detail below.

Figure 6:
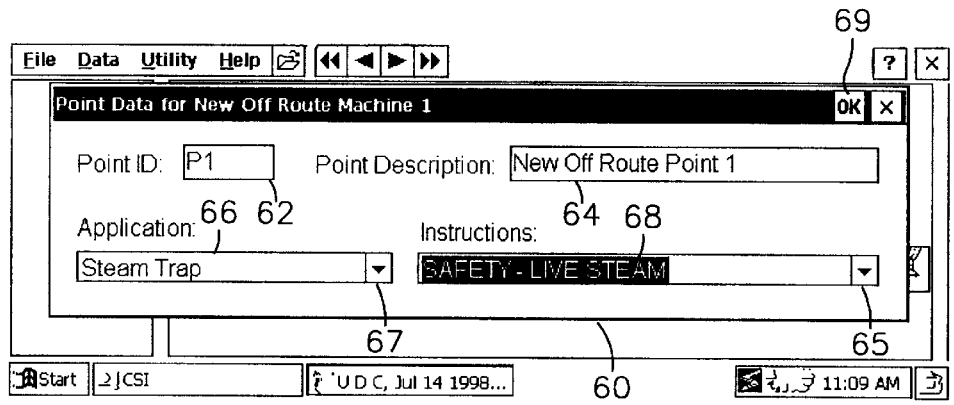
FIG. 6 is a view of a screen showing a Point Data dialog box.

If the user had selected the <New User Defined Machine> option 42 from the dialog box 40 shown in FIG. 4, then when the OK button 56 is pressed, the processor 2 generates a user instruction message in the form of the Point Data dialog box 60 shown in FIG. 6. Since a single machine may contain several points to be tested, the Point Data dialog box 60 allows the user to enter information that is specific to each particular point to be tested. For example, ultrasonic measurement parameters can be setup for each individual valve on a multivalve machine.

As shown in FIG. 6, the dialog box 60 includes a Point ID input box 62 and a Point Description input box 64, each box having a default string of characters. The user may change the default identification code or the default description by typing in new strings of characters using the user input device 6.

The dialog box 60 also includes an Application selection box 66. The Steam Trap application is the only one shown in FIG. 6. However, if the user presses the down arrow 67, the other available applications would appear in list form in the selection box 66. The other available applications include Leak Detection, Mechanical, Valve, Electrical, and User Defined. Thus, at this point, the user may choose between several different application options. The subsequent measurement parameter setup options presented to the user from this point onward will vary depending upon which application the user chooses at the Application selection box 66.

The "Instructions" listed in the box 68 will depend upon the application chosen in the selection box 66. The box 68 provides the user with application-specific instructions and warnings associated with the selected measurement application. If the instructions do not fit completely within the box 68, the box 68 may be expanded by pressing the down arrow 65.

If the user chooses the Steam Trap application at the selection box 66, then a first user input signal is generated by the user input device 6. When the processor 2 receives the first user input signal, the processor 2 generates a user instruction message in the form of the Steam Trap Data dialog box 70 shown in FIG. 7. The Steam Trap Data dialog box 70 allows the user to enter identification information and select measurement parameters and alarm limits that are specific to the ultrasonic monitoring of a steam trap.

Figure 7:
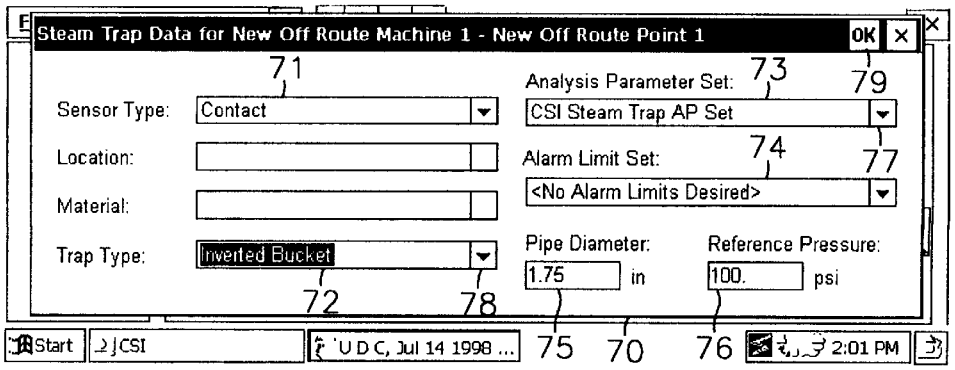
FIG. 7 is a view of a screen showing a Steam Trap Data dialog box.

The Steam Trap Data dialog box 70 includes the Sensor Type selection box 71, which allows the user to choose between a contact sensor and an airborne sensor. The airborne sensor is a piezoelectric transducer that receives ultrasonic sound waves through the air. The contact sensor is a piezoelectric transducer installed at one end of a hollow shaft. The other end of the hollow shaft is placed in contact with the point being monitored, and the ultrasonic sound waves propagate down the shaft to the sensor. These sensor types are described in detail in a pending application (U.S. Ser. No. 09/073,276, filed May 5, 1998). As shown in FIG. 7, the default sensor type for a steam trap measurement is the contact sensor.

The Steam Trap Data dialog box 70 also allows the user to select the analysis parameters to be used while making the ultrasonic measurement on the steam trap. These are the parameters that are ultimately downloaded from the memory 8 over the interface 10 to the ultrasonic measurement instrument 12. As indicated in FIG. 7, when the steam trap application is selected, a default parameter set appears in the Analysis Parameter Set selection box 73. The default set preferably includes $Pk^h$ (a peak-hold measurement corresponding to the peak ultrasonic sound measured during the measurement period selected manually by the user), temperature, and cycle time of the trap. By pressing the down arrow 77, the user may also choose from a list of other parameter sets which include selected combinations of $Pk^h$, $Pk^{factor}$ (the difference between the peak and the average value of the signal during a measurement), Avg (the average value of the ultrasonic signal), Cycle Time, and Temp. Preferably, steam trap measurements include two temperature and two ultrasonic level readings.

Using the Trap Type selection box 72, the user chooses the type of steam trap that will be monitored. As shown in FIG. 7, the default type is inverted bucket. Other steam trap types, which may be selected using the down arrow 78, include float, thermostatic, float/thermostatic, and thermodynamic.

The Alarm Limit Set selection box 70 enables the user to select a particular alarm limit set or choose to use no alarm limits (which is the default option) during the ultrasonic measurement. The Pipe Diameter input box 75 and the Reference Pressure input box 76 allow the user to enter, respectively, the diameter of the pipe associated with the steam trap and the reference pressure of the steam within the pipe.

If the user chooses the Leak Detection application in the Application selection box 66 in FIG. 6, then a second user input signal is generated by the user input device 6. When the processor 2 receives the second user input signal, the processor 2 generates a user instruction message in the form of the Leak Detection Data dialog box 80 shown in FIG. 8. The Leak Detection Data dialog box 80 allows the user to enter identification information and select measurement parameters and alarm limits that are specific to ultrasonic monitoring for the detection of leaks in pipes and fittings.

The Sensor Type selection box 81 allows the user to choose between a contact sensor and an airborne sensor. For leak detection, the default sensor type is the airborne sensor.

Figures 8, 9, 10:
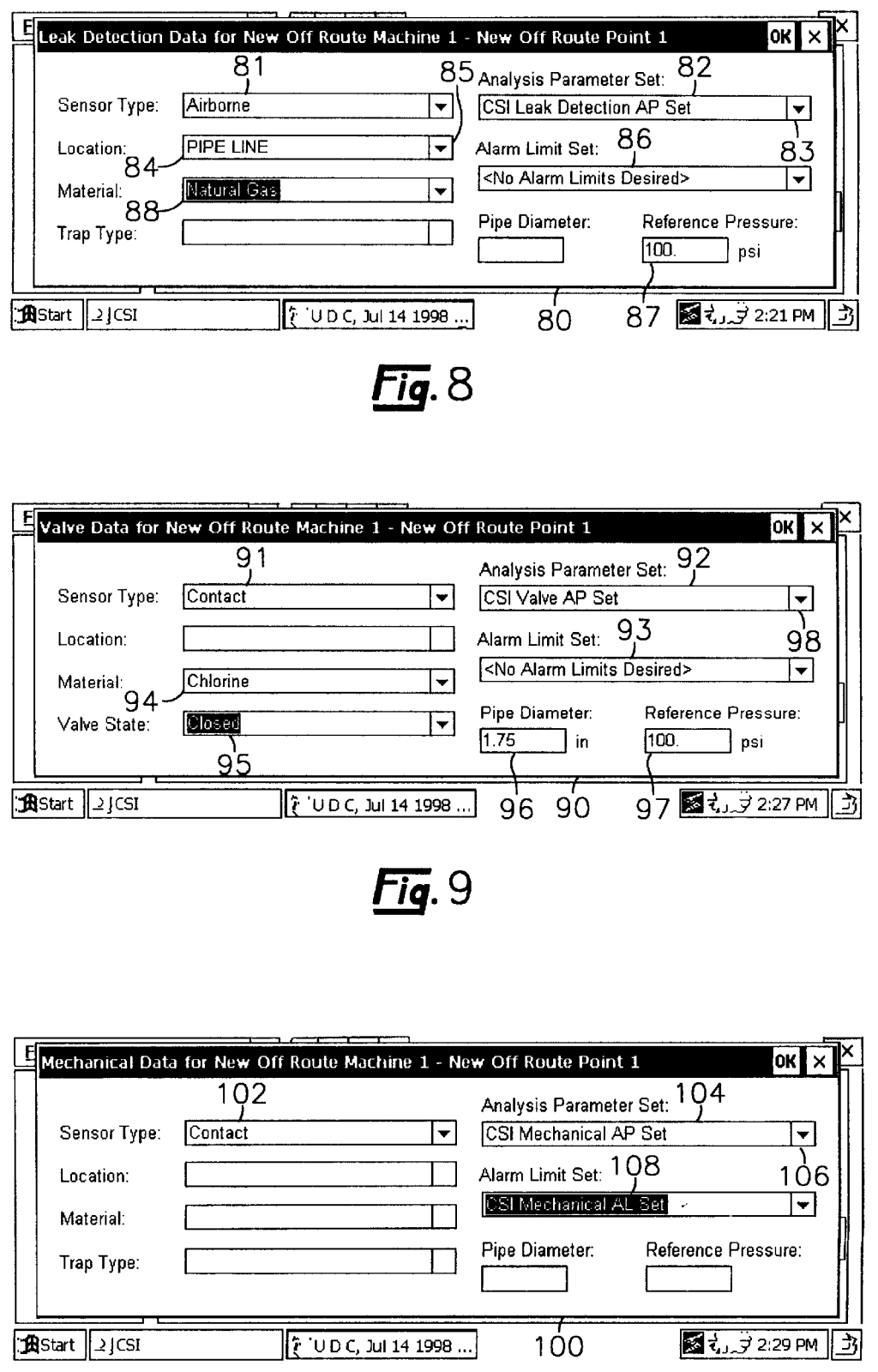

The Analysis Parameter Set selection box 82 allows the user to select the analysis parameters to be used while making the ultrasonic leak detection measurement. As indicated in FIG. 8, when the leak detection application is selected, a default parameter set for leak detection appears in the Analysis Parameter Set selection box 82, which is preferably $Pk^h$ (peak hold). However, by pressing the down arrow 83, the user may choose from a list of other parameter sets which include various combinations of $Pk^h$, $Pk^{factor}$, Avg and Temp.

Using the Location selection box 84, the user may further specify the location of the leak detection measurement. The default location for leak detection is NONE. However, the user may select from a list of previously-defined locations by pressing the down arrow 85. An example of a user-defined location, PIPE LINE, is shown in FIG. 8.

The Alarm Limit Set selection box 86 enables the user to select a particular alarm limit set or choose to use no alarm limits (which is the default option) during the ultrasonic leak detection measurement. The Reference Pressure input box 87 allows the user to enter the reference pressure of the material within the pipe, while the Material input box 88 provides for specifying the material, such as natural gas, flowing in the pipe.

If the user chooses the Valve application at selection box 66 in FIG. 6, then a third user input signal is generated by the user input device 6. When the processor 2 receives the third user input signal, the processor 2 generates a user instruction message in the form of the Valve Data dialog box 90 shown in FIG. 9. The Valve Data dialog box 90 allows the user to enter identification information and select measurement parameters and alarm limits that are specific to the ultrasonic monitoring of valves.

The Sensor Type selection box 91 allows the user to choose between a contact sensor and an airborne sensor. For valve monitoring, the default sensor type is the contact sensor.

The Analysis Parameter Set selection box 92 allows the user to select the analysis parameters to be used while monitoring a valve with the ultrasonic sensing device 12. As indicated in FIG. 9, when the valve application is selected, a default parameter set (preferably $Pk^h$) for valve monitoring appears in the Analysis Parameter Set selection box 92. However, by pressing the down arrow 98, the user may also choose from a list of other parameter sets including various combinations of $Pk^h$, $Pk^{factor}$, Avg and Temp.

The Alarm Limit Set selection box 93 allows the user to select a particular alarm limit set or choose to use no alarm limits (which is the default option) during ultrasonic valve monitoring. The Pipe Diameter input box 96 and the Reference Pressure input box 97 allow the user to enter, respectively, the diameter of the pipe associated with the valve and the reference pressure of the material within the pipe. The Valve State selection box 95 allows the user to specify whether the normal state of the valve is open or closed. The Material selection box 94 provides for specifying the material, such as chlorine, flowing in the pipe.

If the user chooses the Mechanical application at selection box 66, then a fourth user input signal is generated by the user input device 6. When the processor 2 receives the fourth user input signal, the processor 2 generates a user instruction message in the form of the Mechanical Data dialog box 100 shown in FIG. 10. The Mechanical Data dialog box 100 allows the user to enter identification information and select measurement parameters and alarm limits that are specific to the ultrasonic monitoring of rotating components of a machine, such as shafts, gears, and bearings.

Using the Sensor Type input box 102, the user may choose between a contact sensor or an airborne sensor. The contact sensor is the default sensor type for mechanical monitoring.

The Analysis Parameter Set selection box 104 also provides for selection of the analysis parameters to be used with the ultrasonic measurement instrument 12 during mechanical monitoring. As indicated in FIG. 10, when the mechanical application is selected, a default parameter set (preferably $Pk^h$, $Pk^{factor}$, Avg and Temp) for mechanical monitoring appears in the Analysis Parameter Set selection box 104. The user may also choose from a list of other parameter sets (subcombinations of the default set) by pressing the down arrow 106. The Alarm Limit Set input box 108 allows the user to select a particular alarm limit set or choose to use no alarm limits.

If the user chooses the Electrical/Corona application at the Application selection box 66 in FIG. 6, then a fifth user input signal is generated by the user input device 6. When the processor 2 receives the fifth user input signal, the processor 2 generates a user instruction message in the form of the Electrical/Corona Data dialog box 110 shown in FIG. 11. The Electrical/Corona Data dialog box 110 allows the user to enter identification information and select measurement parameters and alarm limits that are specific to the ultrasonic detection of abnormal electrical discharge or corona.

The Sensor Type input box 112 allows the user to choose between a contact sensor and an airborne sensor. For electrical/corona monitoring, the default sensor type is the airborne sensor.

Figure 11:
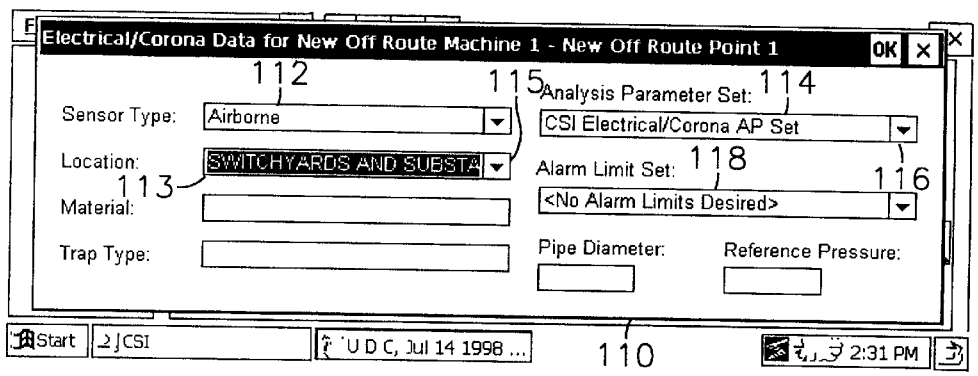
FIG. 11 is a view of a screen showing a Electrical/Corona Data dialog box.

The Analysis Parameter Set selection box 114 allows the user to select the analysis parameters to be used while monitoring electrical discharge or corona with the ultrasonic measurement instrument 12. As indicated in FIG. 11, when the Electrical/Corona application is selected, a default parameter set ($Pk^h$) for electrical/corona monitoring appears in the Analysis Parameter Set selection box 114. By pressing the down arrow 116, the user may also choose from a list of other parameter sets including various combinations of $Pk^h$, $Pk^{factor}$, Avg and Temp.

The Alarm Limit Set selection box 118 allows the user to select a particular alarm limit set or to choose to use no alarm limits (which is the default option) during electrical/corona monitoring. Using the Location input box 113, the user may specify the location of the electrical/corona measurement. The default location for electrical/corona monitoring is NONE. However, the user may select from a list of previously-defined locations by pressing the down arrow 115. An example of a user-defined location, SWITCHYARDS AND SUBSTATIONS, is shown in FIG. 11.

Figure 12:
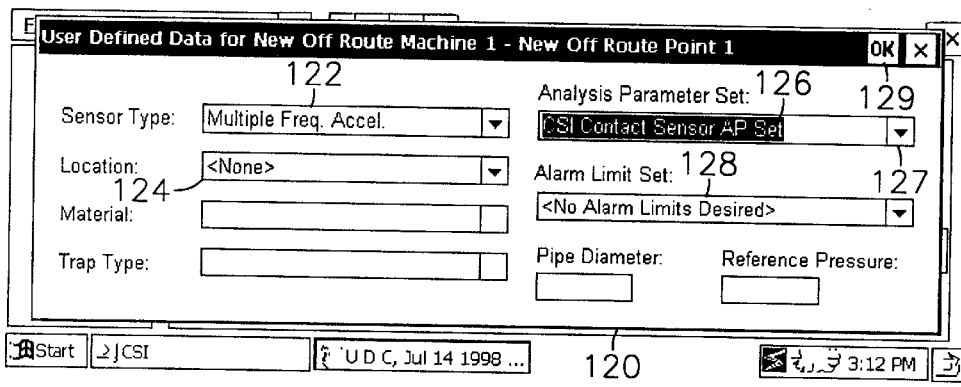
FIG. 12 is a view of a screen showing a User Defined Data dialog box.

If the user chooses the User Defined application at Application selection box 66 in FIG. 6, then a sixth user input signal is generated by the user input device 6. When the processor 2 receives the sixth user input signal, the processor 2 generates a user instruction message in the form of the User Defined Data dialog box 120 shown in FIG. 12. The User Defined Data dialog box 120 allows the user to enter identification information and select measurement parameters and alarm limits that are specific to a user-defined monitoring application using the ultrasonic measurement instrument. Using the Sensor Type selection box 122, the user may choose between the contact and airborne ultrasonic sensors, or other types of sensors, such as accelerometers.

The Analysis Parameters Set selection box 126 provides for selection of the analysis parameters to be used with the ultrasonic sensing device 12 during the user-defined measurement. The user may also choose from a list of other measurement parameter sets as previously described by pressing the down arrow 106. The Alarm Limit Set selection box 128 allows the user to select a particular alarm limit set or choose to use no alarm limits. The user may also define a location for the user-defined measurement using the Location selection box 124.

For the purposes of the remainder of this description, we will assume that the user has selected a steam trap application for an inverted bucket steam trap. With reference to FIG. 7, after the user has completed entering information in the Steam Trap Data dialog box 70, the user presses the OK button 79 in the top right corner. At this point, the processor 2 generates a user instruction message in the form of the screen shown in FIG. 13. This screen summarizes for the user information concerning the currently active measurement point and provides the user with options for how to proceed further.

Figure 13:
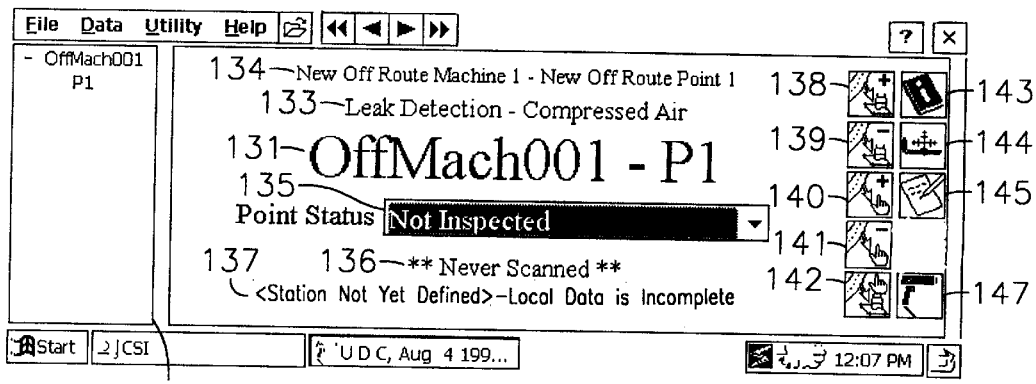
FIG. 13 is a view of the Main screen.

On the left side of the graphic of FIG. 13 is a tree structure 130. The tree structure 130 indicates that a setup has been completed for one measurement point, identified as "P1", on one off-route machine, identified as "OffMach001". P1 is highlighted in the tree structure 130, indicating that P1 is the currently active measurement point. If other measurement points were set up, those points would also be listed in the tree structure 130 under the machine identification. The tree structure 130 allows the user to make any one of the measurement points in the tree the active point by simply highlighting the point identification in the tree structure 130 using the user input device 6.

In the center of the graphic of FIG. 13, in large type, is a field 131 indicating the machine identification and the point identification. Immediately above the field 131 is a field 133 indicating the application type (in this example: "Leak Detection") and the material (in this example: "compressed air"). Immediately above that is a field 134 indicating the machine description and the point description for the currently active measurement point. Immediately below the machine and point identifications field 131 is a Point Status field 135 currently indicating that the point has not yet been inspected. Immediately below the Point Status field 135 is a previous status field 136. If the currently active point had been previously tested, the previous status field 136 would indicate the time, date, and status of the most recent test. Since the currently active measurement point has just been set up and has not yet been tested, the previous status field 136 indicates that the point was "Never Scanned."

Immediately below the test status field 136 is the station and route field 137. Since the just-completed operation has identified measurement parameters for an off-route machine, no station and route has yet been identified for this machine. Thus, the station field indicates "Station Not Yet Defined", and the route field indicates "Local Data." "Local Data" here indicates that the defined measurement parameters are not yet associated with any particular route, and are therefore "local" to the particular machine. When the measurement parameters and data for this measurement point are later dumped to the central computer 14, the operator will assign the parameters to a particular station and route within a database on the central computer 14.

On the right side of the graphic shown in FIG. 13 is a cluster often buttons in two columns. The top button in the left column is the Add Machine button 138. The user would press the button 138 to set up a new measurement point on yet another off-route machine. When the user presses the button 138, the processor 2 generates a user instruction message in the form of the screen shown in FIG. 4. The user would then proceed to define the new machine according to the procedure previously described.

Immediately below the button 138 is the Remove Machine button 139. The user would press the button 139 to remove the current machine (and all measurement points on that machine) from the tree structure 130 and to remove any setup information related to the current machine from the memory 8.

Immediately below the button 139 is the Add Point button 140. The user would press the button 140 to set up a new measurement point on the current machine. When the user presses the button 140, the processor 2 generates a user instruction message in the form of the screen shown in FIG. 6. The user would then proceed to define the new measurement point according to the procedure previously described.

Immediately below the button 140 is the Remove Point button 141. The user would press the button 141 to remove the current measurement point from the tree structure 130 and to remove any setup information related to the current measurement point from the memory 8.

The bottom button in the left column is the Edit button 142. The user would press the button 142 to modify any of the identification information or measurement parameters, or alarm limits, associated with the current measurement point on the current machine. When the user presses the button 142, the processor 2 generates n user instruction message in the form of the screen shown in FIG. 5. The user would then proceed to modify the current machine and measurement point setup according to the procedure previously described for setting up a new measurement point.

Figure 14:
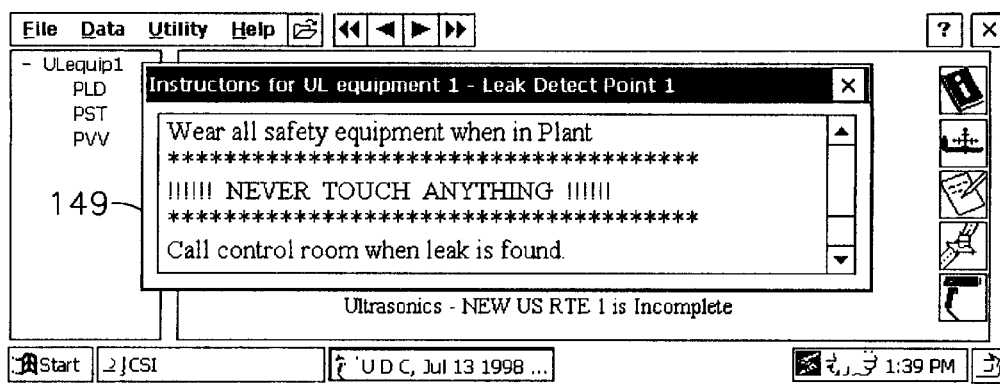
FIG. 14 is a view of a screen showing an Instructions dialog box.

With continued reference to FIG. 13, the top button in the right column at the right side of the screen is the Instructions button 143. When the user presses the Instructions button 143, the processor 2 generates a user instruction message in the form of the Instructions dialog box 149 shown in FIG. 14. The Instructions dialog box 149 provides information concerning the proper way to make the measurement for the current measurement point. If it is imperative that the user read the instructions before making the measurement, say for safety considerations, then all input boxes for the measurement point will be disabled until the instructions have been read.

Figure 15:
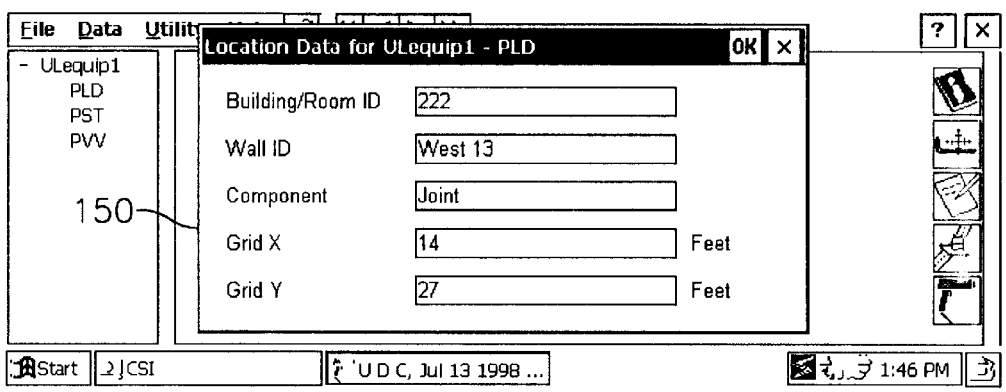
FIG. 15 is a view of a screen showing a Location Data dialog box.

Immediately below the Instructions button 143 is the Location button 144. When the user presses the button Location button 144, the processor 2 generates a user instruction message in the form of the Location dialog box 150 shown in FIG. 15. The Location dialog box 150 allows the user to enter detailed information to more precisely define the location of a non-discrete measurement point.

Figure 16:
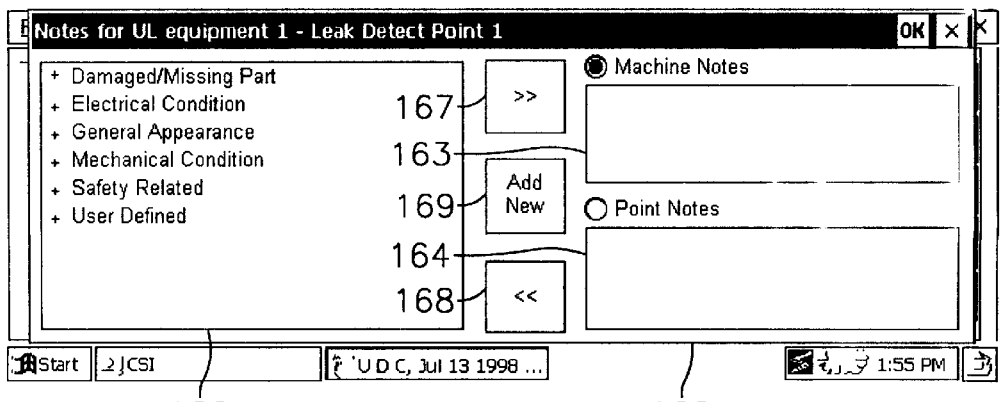
FIG. 16 is a view of a screen showing a Notes dialog box.

Immediately below the Location button 144 is the Notes button 145. When the user presses the Notes button 145, the processor 2 generates a user instruction message in the form of the Notes dialog box 160 shown in FIG. 16. The Notes dialog box 160 allows the user to enter both predefined and user-defined notes for the machine and the measurement point. On the left side of the Notes dialog box 160 is a notes tree 162 that includes all predefined notes as well as any user defined notes. The predefined notes are those that are contained in the setup file selected at the screen shown in FIG. 3. User-defined notes are those that a user enters in the field as described below. Shown in FIG. 16 are five predefined notes categories and one category for user-defined notes. To gain access to the notes for any particular category, the user clicks on the category using the user input device 6.

At the top right corner of the Notes dialog box 160 is the Machine Notes input box 163, and at the bottom right is the Point Notes input box 164. The user can make either box the "active" box by pressing the radio button 165 for the Machine Notes or the radio button 166 for the Point Notes. The user assigns a note to one of the boxes 163 or 164 by either double-clicking on a note in the notes tree 162, or by highlighting a note in the notes tree 162 and then pressing the add-note button 167. The highlighted note will then appear in whichever notes box is active. Likewise, the user can remove a note from the active notes box by either double clicking on the note, or by highlighting the note and then pressing the remove-note button 168.

Figure 17:
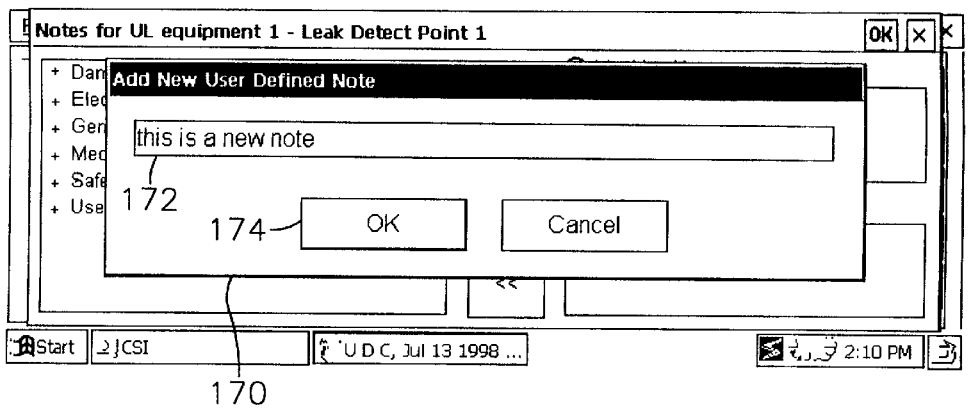
FIG. 17 is a view of a screen showing a n Add New User Defined Note input box.

To add a new user-defined note to the notes tree 162, the user presses the Add New button 169. When the user presses the Add New button 169, the processor 2 generates a user instruction message in the form of the "Add New User Defined Note" dialog box 170 shown in FIG. 17. The user can then compose a new note by typing it in to the new note input box 172. When the user presses the OK button 174, the new note is added to the memory 8 and appears graphically in the notes tree 162 under the User Defined category. The new user-defined note is also placed into the active notes box on the right side of the Notes dialog box 160. In a preferred embodiment of the invention, the user-defined notes may be a maximum of 40 characters in length, and there may be up to 24 user-defined notes stored in the memory 8.

Figure 18:
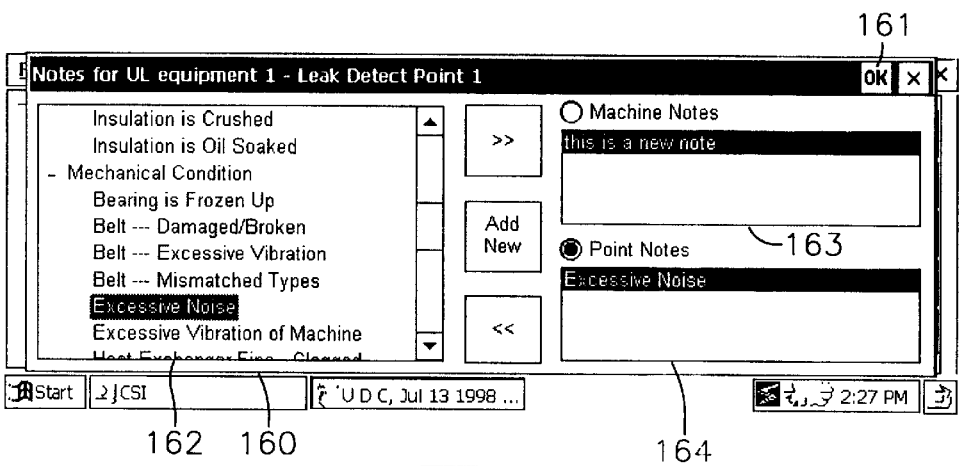
FIG. 18 is a view of a screen showing a Notes dialog box with newly-added notes.

FIG. 18 shows the Notes dialog box 160 after the user has entered a user-defined note into the Machine Notes input box 163, and an "Excessive Noise" note (from the Mechanical Condition category) into the Point Notes input box 164. In a preferred embodiment, any or all of the notes may be assigned as either machine or point notes. When the user has finished entering notes, the user presses the OK button 161 to return to the screen shown in FIG. 13.

Figure 19:
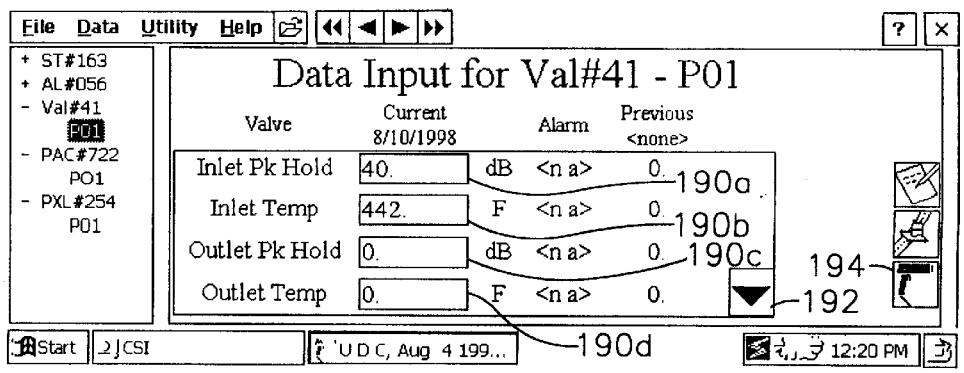
FIG. 19 is a view of a Data Input screen for a measurement point.

Below the Notes button 145 in FIG. 13 is the Gun button 147. The Gun button 147 allows the user to toggle between the Main screen as shown in FIG. 13 and the Data Input screen represented in FIG. 19. As shown in FIG. 19, the Data Input screen provides parameter value input boxes 190a, 190b, 190c, and 190d in which the measured values are shown. The user may change these values by typing in new values in the input boxes. If a particular measurement application has more than the four parameters that will fit at one time on the Data Input screen, arrow buttons 192 are provided (either an up-arrow or a down-arrow as necessary) to allow the user to scroll to reveal other parameter values. The user may return to the Main screen by pressing the Gun button 194.

When the user has completed entering the measurement information in the previously described screens, the setup device 1 is ready to make the measurement parameters and alarm limits for the currently active point available to the ultrasonic sensing device 12. As discussed previously, the measurement point shown in field 131 of the screen shown in FIG. 13 is the currently active point. Before downloading the measurement parameters and alarm limits from the setup device 1 to the ultrasonic sensing device 12, the user should first verify that the measurement point listed in the field 131 is the point that the operator wishes to test.

To download the parameters, the operator selects the appropriate function on the ultrasonic sensing device 12 to cause the ultrasonic sensing device 12 to send a parameter request signal to the interface 10 of the setup device 1. In the preferred embodiment, the parameter request signal is an infrared signal. When the interface 10 receives the parameter request signal from the ultrasonic sensing device 12, the interface transfers the signal to the processor 2. The processor 2 then transfers the ultrasonic measurement parameters and alarm limits for the currently active point from the memory 8 to the interface 10. The ultrasonic measurement parameters and alarm limits are then transferred over the interface 10 to the ultrasonic sensing device 12.

It is contemplated, and will be apparent to those skilled in the art from the preceding description and the accompanying drawings that modifications and/or changes may be made in the embodiments of the invention. For example, in the preferred embodiment, the setup device 1 is contained in a housing separate from the ultrasonic sensing device 12. However, it will be appreciated that the setup device 1 and the ultrasonic sensing device 12 could also be contained within the same portable housing.

Further, it will be appreciated that the size and arrangement of components of the setup device 1 is not limited to that of a PDA-type device. The invention could also be implemented in a lap-top or palm-top computer, or in a desktop-sized personal computer. Also, the available physical devices and parameters to be measured could vary.

Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. An apparatus for determination of ultrasonic measurement parameters for ultrasonic measurements to be performed on a system, the ultrasonic measurements to be performed using a portable ultrasonic measurement device, the ultrasonic measurement parameters comprising information used in configuring the portable ultrasonic measurement device to make the ultrasonic measurements on the system, where the ultrasonic measurement device uses an ultrasonic sensor to measure ultrasonic characteristics of the system, the ultrasonic characteristics being indicative of an operating condition of the system, the apparatus comprising:

a processor for generating user instruction messages corresponding to a plurality of different application types, the instruction messages querying a user of the apparatus concerning which of the application types are applicable to the system on which the ultrasonic measurements are to be performed and offering the user a choice of application type selected from the group comprising steam trap, leak detection, valves, mechanical, electrical, and user-defined, and providing response options from which the user chooses in selecting from among the plurality of application types;

a graphical user interface connected to the processor, the graphical user interface comprising:
      a display device for receiving the user instruction messages generated by the processor, and visually displaying the user instruction messages to the user, and
      a user input device for enabling the user to enter responses to the user instruction messages, and for generating user input signals based upon the responses to the user instruction messages, the user input signals including an application type signal indicating the specific application type that is applicable to the system on which measurements are to be performed;

the processor for receiving the user input signals and generating the ultrasonic measurement parameters based on the user input signals;

memory connected to the processor for receiving and storing the ultrasonic measurement parameters; and a data interface connected to the processor for receiving the at least one set of the ultrasonic measurement parameters from the processor, and for providing the at least one set of the ultrasonic measurement parameters to the portable ultrasonic measurement device.

2. The apparatus of claim 1 wherein the data interface is further operable to make a data interface connection with an external computer for transferring the set of ultrasonic measurement parameters from the apparatus to the external computer, and from the external computer to the apparatus.

3. The apparatus of claim 1 wherein the processor further generates identification information based on the user input signals, the identification information identifying a particular system on which the ultrasonic measurements are to be made, and identifying a point on the particular system where the ultrasonic measurements are to be made.

4. The apparatus of claim 1 wherein the processor further generates user instruction messages that provide information to the user concerning the ultrasonic measurements to be performed on the system.

5. The apparatus of claim 1 wherein the user input device comprises a keyboard.

6. The apparatus of claim 1 wherein the user input device comprises a touch screen.

7. The apparatus of claim 1 wherein the processor, graphical user interface, data interface, and memory are disposed within a hand-held portable unit.

8. The apparatus of claim 1 wherein the data interface further comprises a wireless infrared data interface.

9. A method for determining ultrasonic measurement parameters for ultrasonic measurements to be performed on a system, the ultrasonic measurements to be performed using an ultrasonic measurement device, where the ultrasonic measurement device uses an ultrasonic sensor to measure ultrasonic characteristics of the system, the ultrasonic characteristics being indicative of an operating condition of the system, the method comprising:

(a) querying a user concerning which of a plurality of application types are applicable to the system on which the ultrasonic measurements are to be performed;

(b) providing response options from which the user chooses in responding to the querying of step (a), which includes offering the user a choice of application type selected from the group consisting of steam trap, leak detection, valves, mechanical, electrical, and user-defined;

(c) receiving user responses to the querying of step (a) that identify which of the plurality of application types is applicable to the system;

(d) generating at least one set of the ultrasonic measurement parameters based on the user responses; and (e) storing and selectively outputting the set of ultrasonic measurement parameters.

10. The method of claim 9 further comprising:

(f) based on the chosen application type, querying the user concerning analysis parameters applicable to the system on which the ultrasonic measurements are to be performed;

(g) receiving user responses to the querying of step (f) concerning analysis parameters applicable to the system; and (h) generating the at least one set of the ultrasonic measurement parameters based on the user responses received in step (g).

11. The method of claim 9 further comprising:

(f) generating a machine identifier for identifying the system;

(g) associating the set of ultrasonic measurement parameters with the machine identifier;

(h) storing the machine identifier in a measurement setup device;

(I) establishing a data interface between the measurement setup device and the ultrasonic measurement device;

(j) sending a parameter request across the data interface from the ultrasonic measurement device to the measurement setup device to request a download of the set of ultrasonic measurement parameters;

(k) transferring the set of ultrasonic measurement parameters from the measurement setup device across the data interface to the ultrasonic measurement device in response to the parameter request; and (l) configuring the ultrasonic measurement device to take measurements on the system based on the set of ultrasonic measurement parameters.

12. An apparatus for determination of ultrasonic measurement parameters for ultrasonic measurements to be performed on a system, the ultrasonic measurements to be performed using an ultrasonic measurement device, the ultrasonic measurement parameters comprising information used in configuring the ultrasonic measurement device to make the ultrasonic measurements on the system, where the ultrasonic measurement device uses at least an ultrasonic sensor to measure ultrasonic characteristics of the system, the ultrasonic characteristics being indicative of an operating condition of the system, the apparatus comprising:

a processor for generating user instruction messages corresponding to a plurality of different application types, the instruction messages querying a user of the apparatus concerning which of the application types are applicable to the system on which the ultrasonic measurements are to be performed, and providing response options from which the user chooses in selecting from among the plurality of application types, wherein the processor generates the user instruction messages offering the user a choice of application type selected from the group comprising steam trap, leak detection, valves, mechanical, electrical, and user-defined;

a user communication device connected to the processor for receiving the user instruction messages generated by the processor, and communicating the user instruction messages to the user;

a user input device connected to the processor for enabling the user to choose from among the response options, and for generating user input signals based upon response options chosen by the user, the user input signals including an application type signal indicating the specific application type that is applicable to the system on which measurements are to be performed;

the processor for receiving the user input signals and generating at least one set of the ultrasonic measurement parameters based on the user input signals; and memory connected to the processor for receiving and storing the set of ultrasonic measurement parameters.

13. The apparatus of claim 12 further comprising:

the processor further for generating additional user instruction messages that are specific to the application type indicated by the application type signal, the additional user instruction messages providing the user a plurality of choices and queries that are specific to the application type, the instruction messages further querying the user concerning analysis parameters applicable to the system on which the ultrasonic measurements are to be performed;

the user communication device being responsive to the additional user instruction messages to display to the user the plurality of choices and queries concerning the analysis parameters; and the user input device for generating the user input signals indicating the analysis parameters applicable to the system on which the ultrasonic measurements are to be performed.

14. The apparatus of claim 13 further comprising:

the processor further for generating the additional user instruction messages specific to the application type, the instruction messages further querying the user concerning the analysis parameters selected from the group including a peak-hold analysis parameter, an average value analysis parameter, a peak-minus-average analysis parameter, and a cycle time analysis parameter, where the peak-hold analysis parameter specifies that a peak ultrasonic value measured during a measurement period is to be recorded, where the average value analysis parameter specifies that an average value of ultrasonic measurements made during the measurement period is to be recorded, where the peak-minus-average analysis parameter specifies that a difference between the peak ultrasonic value and the average value is to be recorded, and where the cycle time analysis parameter specifies that a cycle time of a steam trap is to be recorded.

15. The apparatus of claim 14 further comprising the processor for generating the additional user instruction messages indicating to the user that the peak-hold analysis parameter and the cycle time analysis parameter are default analysis parameters when the user chooses the steam trap application type.

16. The apparatus of claim 14 further comprising the processor for generating the additional user instruction messages indicating to the user that the peak-hold, average, and peak-minus-average analysis parameters are default analysis parameters when the user chooses the mechanical application type.

17. The apparatus of claim 14 further comprising the processor for generating the additional user instruction messages indicating to the user that the peak-hold analysis parameter is a default analysis parameter when the user chooses the leak detection application type.

18. The apparatus of claim 12 further comprising a data interface connected to the processor for receiving the at least one set of the ultrasonic measurement parameters from the processor, and for providing the at least one set of the ultrasonic measurement parameters to the ultrasonic measurement device.

19. The apparatus of claim 18 wherein the data interface is further operable to make a data interface connection with an external computer for transferring the set of ultrasonic measurement parameters from the apparatus to the external computer, and from the external computer to the apparatus.

20. The apparatus of claim 12 wherein the processor further generates identification information based on the user input signals, the identification information identifying a particular system on which the ultrasonic measurements are to be made, and identifying a point on the particular system where the ultrasonic measurements are to be made.

21. The apparatus of claim 12 wherein the user input device comprises a graphical user interface.

22. The apparatus of claim 12 wherein the processor, user communication device, user input device, interface, and memory are disposed within a hand-held portable unit.

* * * * *